United States Patent
Watson (12) United States Patent (10) Patent No.: US 6,539,944 B1
(45) Date of Patent: Apr. 1, 2003

(54) DETHROMBOSIS FACILITATED BY VASODILATION

(76) Inventor: Brant D. Watson, 855 Euclid Ave., #407, Miami Beach, FL (US) 33139

( * ) Notice: Subject to any disclaimer, the term of this patent is extended or adjusted under 35 U.S.C. 154(b) by 0 days.

(21) Appl. No.: 09/592,610

(22) Filed: Jun. 12, 2000

Related U.S. Application Data (60) Provisional application No. 60/138,609, filed on Jun. 11, 1999.

(51) Int. Cl.$^7$ ............................................. A61B 19/00
(52) U.S. Cl. ............................. 128/898; 606/7; 607/89
(58) Field of Search .............................. 606/2, 3, 7, 15, 606/16; 607/88, 89; 128/898

(56) References Cited

U.S. PATENT DOCUMENTS

| | | | |
|---|---|---|---|
| 5,053,006 A | 10/1991 | Watson | 604/52 |
| 5,354,324 A | * 10/1994 | Gregory | 607/92 |
| 5,571,151 A | * 11/1996 | Gregory | 607/88 |
| 5,573,531 A | * 11/1996 | Gregory | 606/14 |
| 5,649,923 A | 7/1997 | Gregory et al. | 606/15 |
| 5,662,590 A | 9/1997 | de la Torre et al. | 601/2 |
| 5,671,314 A | 9/1997 | Gregory et al. | 385/128 |
| 5,817,144 A | * 10/1998 | Gregory | 606/89 |
| 6,022,309 A | * 2/2000 | Celliers et al. | 66/7 |
| 6,106,546 A | * 8/2000 | Gregory | 607/89 |
| 6,117,128 A | * 9/2000 | Gregory | 606/7 |

OTHER PUBLICATIONS

Morimoto et al, "Possible Mechanisms of Vascular Relaxation Induced by Pulsed–UV Laser", Photochemistry and Photobiology, 68(3), pp 386–393, 1998.*

Possible Mechanisms of Vascular Relaxation Induced by pulsed–UV Laser, Morimoto Y; Arai T; Matsuo H; Kikuchi M, Photochemistry and Photobiology 1998 Sep;68(3):388–93.

Putaminal haemorrage after recanalization of an embolic MCA occlusion treated with tissue plasminogen activator, H. Bruckmann and A. Ferbert, Neuroradiology (1989) 31:95–97.

Comparative Pharmacology of Site Directed Antithrombin Agents. Implication in Drug Development, Demetra Callas and Jawed Fareed, Thrombosis and Haemostasis—F.K. Schattauer Verlagsgesellsccchaft mbH (Stuttgart) 74(1) 473–481 (1995).

Reversibility of platelet thrombosis in vivo. Quantitative analysis in porcine carotid arteries, Wysokinski W., McBane R., Chesebro J.H., Owen W.G., Thromb Haemost 1996 Dec:76(6)1108–13.

Endothelium–Derived Relaxing Factor Modulates Platelet Aggregation in an In Vivo Model of Recurrent Platelet Activation, Paolo Golino, Maurizio Capelli–Bigazzi, Giuseppe Ambrosio, Massim Ragni, Enrico Russolillo, Mario Condorelli, and Massimo Chairello, Circulation Research vol. 71, No. 6:1447–1456.

Photochemical Generation of Nitric Oxide From Nitro–Containing Compounds: Possible Relation to Vascular Photorelaxation Phenomena, John Anthony Bauer and Ho–Leung Fung, Life Sciences, vol. 54, pp. PL 1–4.

(List continued on next page.)

*Primary Examiner*—Michael Peffley
(74) *Attorney, Agent, or Firm*—Banner & Witcoff, Ltd.

(57) ABSTRACT

Methods are presented for the dissolution of a thrombus which occludes a blood vessel. The methods utilize the vasodilation effect produced by irradiating a blood vessel with UV laser light. The laser-induced vasodilation leads to stretching of the occluding thrombus, which becomes infiltrated with blood and quickly dissolves without the emission of emboli. Some of the methods involve combination of UV laser irradiation with thrombolytic agents, dethrombosing agents, or antiplatelet agents to enhance their effectiveness and reduce side effects.

43 Claims, 7 Drawing Sheets

OTHER PUBLICATIONS

Involvement of nitrosothiols, nitric oxide and voltage–gated K+ channels in photorelaxation of vascular smooth muscle, Fina Lovren, Chris R. Triggle, European Journal of Pharmacology 347 (1998) pp. 215–221.

Percutaneous Delivery of Low–Level Laser Energy Reverses Histamine–Induced Spasm in Atherosclerotic Yucatan Microswine, Dow Gal, DVM; Saurabh K. Chokshi, M.D.; Morris Mosseri, M.D.; Richard H. Clarke, PhD; and Jeffrey M. Isner, M.D., Circulation vol. 85, No. 2 Feb. 1992 pp. 756–768.

Tissue Plasminogen Activator For Acute Ischemic Stroke, The New England Journal of Medicine, vol. 333 No. 24 Dec. 14, 1995, pp. 1581–87.

Recombinant Tissue Plasminogen Activator in Acute Thrombotic and Embolic Stroke, del Zoppo et al., 84 Annals of Neurology vol. 32, No. 1, Jul. 1992, pp. 78–85.

Relaxation of Vascular Smooth Muscle Induced by Low–PowerLaser Radiation, Hina Chaudhry et al., Photochemistry and Photobiology, vol. 58, No. 5, pp. 661–669.

Characterization of Pulsed–Dye Laser–Mediated Vasodilatation in a Rabbit Femoral After Model of Vasoconstriction, Robert H. Schwengel, et al., Lasers in Surgery and Medicine 13:284–295 (1993).

BCH–2763, a Novel Potent Parenteral Thrombin Inhibitor, Is an Effective Antithrombotic Agent in Rodent Models of Arterial and Venous Thrombosis—Comparisons with Heparin, r–Hiroudin, Hirulog, Inogatran and Argatroban, Carolyn D. Finkle et al., Thromb Haemost 1998, 79:431–8.

Acute Results, Complications, and Effect of Lesion Characteristics on Outcome With the Solid–State, Pulsed–Wave, Mid–Infrared Laser angioplasty System: Final Multicenter Registry Report, On Topaz et al., Lasers in Surgery and Medicine 22:228–239 (1998).

Plaque Removal and Thrombus Dissolution with the Photoacoustic Energy of Pulsed–Wave Lasers–Biotissue Interactions and Their Clinical Manifestations, On Topaz et al., General Cardiology, Review 1996 87:384–391.

Photothrombotic Occlusion of Rat Middle Cerebral Artery: Histopathological and Hemodynamic Sequelae of Acute Recanalization, Histoshi Nakayama et al., Journal of Cerebral Blood Flow and Metabolism 8:357–366 1988.

Stroke and Cerebral Circulation, Oral Presentations, Abstracts Program, American Heart Association, Feb. 4–6, 1999.

Q–switched ND:YAG laser irradiation at 355 nm mediates rapid focal dilation of a rat middle cerebral artery, Watson, B.D., et al., Soc. Neurosci Abst 24 (part 1):1171, 1998.

Reperfusion and its injury characteristics in an ultraviolet laser–mediated reversible model of photothrombotic stroke, B.D. Watson, et al., Journal of Cerebral Blood Flow and Metabolism, vol. 19, Suppl. 1, 1999, Presented at meeting, (Jun. 13–17, 1999).

Repriming of Vascular Smooth Muscle Photorelaxation is Dependent upon Endothelium–derived Nitric Oxide, I.L. Megson, et al., Endothelium, 1995, vol. 3, pp. 39–46.

* cited by examiner

DETHROMBOSIS FACILITATED BY VASODILATION

This application claims the benefit of U.S. Provisional Application No. 60/138,609, filed Jun. 11, 1999, which is hereby incorporated by reference in its entirety.

TECHNICAL FIELD OF THE INVENTION

The invention is related to thrombus dissolution and thrombolysis. In particular it is related to the use of lasers and pharmaceutical agents to dissolve an occlusive thrombus in a blood vessel by inducing vasodilation in the vicinity of the thrombus.

BACKGROUND OF THE INVENTION

Four approaches are currently available or under development for the treatment of stroke, myocardial infarction, and other vascular occlusive disorders: (1) the use of high-intensity pulsed lasers to disrupt a thrombus or embolus by either ablation or photoacoustic shock; (2) catheterization, angioplasty, and stent emplacement to physically rupture a thrombus or enlarge the vascular lumen adjacent to an atheroma; (3) the administration of thrombolytic or dethrombosing agents to chemically dissociate a thrombus, often followed by administration of platelet inhibitors (also known as antiplatelet agents) to prevent rethrombosis; and (4) thrombectomy, in which a thrombus or atheroma is mechanically minced and removed. Each of these methods is associated with potential harmful effects or poor efficacy in some circumstances.

High peak intensity, high energy fluence pulsed-wave lasers are capable of ablating or dissolving thrombi as a result of the transduction of laser light into acoustical, mechanical, chemical, or thermal energy (Topaz, 1996, 1998). In addition to chemical degradation caused by the absorption of laser light in the ultraviolet (UV), visible, or infrared wavelengths, the ablation technique creates tiny gas bubbles within the thrombus which aid in its disruption. In the photoacoustic approach, the thrombus is destroyed by shock waves transmitted to it via a cavitation bubble which forms at the tip of the catheter that delivers the laser beam. While these methods can be effective, they carry several risks. The high pressure which builds up inside an irradiated thrombus can cause it to fragment, producing distal emboli that pose a significant danger to the patient in the form of secondary occlusions or strokes. If such high-power laser pulses (energy fluence of 300 mJ/mm$^2$) are misdirected toward the vessel wall, they can produce intense shock waves resulting in permanent tissue damage, acute vessel closure, and dissections and perforations of the vessel (Topaz 1996, 1998). These are potentially life-threatening side effects which are not infrequent. For example, the arterial dissection rate is 13–17% in patients treated with pulsed-wave lasers (Topaz 1994; Litvack et al., 1994). A recent improvement in this approach was presented by Buckley et al. (1999), who used a 577 nm pulsed dye laser with an energy fluence of 10 mJ/mm$^2$ to debulk colored (red) thrombi; white thrombi, composed of aggregated platelets or platelets and fibrin, are unlikely to be affected by this treatment.

Balloon angioplasty is generally successful in restoring patency of an artery occluded by atheromatous tissue, but the results are often suboptimal with a large atheroma. Furthermore, because of the tendency for regrowth of atheromatous tissue at the site of injury resulting from an angioplasty procedure, the rate of restenosis is typically 50–60% within six months. Laser angioplasty, in which an atheroma is ablated by direct high-intensity irradiation, has a similar restenosis rate. Laser angioplasty also carries the risk of damage to the vessel wall from heat generated within the irradiated atherosclerotic plaque.

Tissue plasminogen activator (t-PA) therapy is considered beneficial for acute myocardial infarction and stroke. Fibrin-rich red thrombi are lysable by thrombolytic agents such as t-PA and urokinase, as are white platelet-fibrin thrombi, which structurally resemble those observed in the clinic after plaque rupture (Davies and Thomas, 1985; Fernandez-Ortiz et al., 1994). In contrast, occlusive fibrin-free white thrombi, consisting solely of aggregated platelets cross-linked by GPIIb-IIIa receptor-mediated fibrinogen bridges, are resistant to lysis by t-PA. Thrombolytic drugs achieve vessel patency in only 75% of cases of acute myocardial infarction (Topaz, 1996), and considerably less in the case of stroke (del Zoppo, 1992). Thrombolytic drugs are associated with an elevated bleeding risk and sometimes leave a residual narrowing at the site of the thrombus. Another area of pharmacological intervention is the use of platelet inhibitors (antiplatelet agents). The prevention of refractory platelet thrombi is of much commercial interest. A major effort is underway to develop RGD (arginine-glycine-aspartic acid) antagonists which inhibit platelet binding mediated by intraplatelet fibrinogen bridges between GPIIb-IIIa membrane receptors (Mousa et al., 1994). These drugs are intended to mitigate residual thrombogenicity of the vascular wall, which often results from incomplete removal of the thrombus following treatment with thrombolytic agents such as t-PA.

Also under commercial development are dethrombosing agents, intended especially for use on thrombi with a high platelet content. These can be natural enzymes such as hirudin from the medicinal leech, the synthetic compound argatroban, and many similar drugs. All of these substances inhibit thrombin, an enzyme required for stabilization of platelet aggregates. If thrombin activity in a thrombus can be inhibited, dethrombosis (release of individual platelets) and subsequent dissolution of the thrombus may result (Wysokinski et al, 1996)

There is a need in the art for additional means for disrupting thrombi so that thrombi resistant to current techniques or whose removal entails undesirable side effects can be treated successfully.

SUMMARY OF THE INVENTION

It is an object of the invention to provide methods for dissolving a thrombus in a blood vessel of a mammal. This and other objects of the invention are provided by one or more of the embodiments described below.

One embodiment of the invention provides a method for dissolving a thrombus in a blood vessel of a mammal. An ultraviolet (UV) laser beam is directed onto the internal or external surface of the blood vessel. The laser beam is directed onto the vessel wall within about 10 vessel diameters of the thrombus, but does not impinge on the thrombus. Subsequent to illuminating the vessel with the laser beam, the thrombus dissolves.

Another embodiment provides another method for dissolving a thrombus in a blood vessel of a mammal. A pharmacological agent which aids in thrombus dissolution is administered to the mammal, and a UV laser beam with an is directed onto blood vessel. The laser beam is directed onto the vessel wall within about 10 vessel diameters of the thrombus, but does not impinge on the thrombus. Either a direct beam or a beam transmitted through an optical fiber can be used. Subsequent to illuminating the vessel with the laser beam, the thrombus dissolves.

Yet another embodiment provides another method for dissolving a thrombus in a blood vessel of a mammal. A UV laser beam is directed onto the thrombus using an optical fiber or liquid core optical guide. In this method, the laser beam does not ablate or photoacoustically shock the thrombus. Subsequent to illuminating the thrombus, the thrombus dissolves.

These and other embodiments of the invention provide the art with new techniques for treating diseases associated with blood vessel occlusive thrombi.

DETAILED DESCRIPTION OF THE INVENTION

The inventor has discovered that when a low intensity ultraviolet (UV) laser beam is directed onto the wall of a blood vessel at a position near an occluding thrombus, vasodilation is induced which leads to stretching of the thrombus and eventual dissolution of the thrombus with no detectable emission of emboli. The efficiency of this effect can be enhanced by coadministration of pharmacologic agents such as thrombolytic agents, dethrombosing agents, or platelet inhibitors.

The invention is useful for removing vascular obstructions composed of organized aggregations of circulating blood elements, e.g., platelets and erythrocytes combined with cross-linking substances such as fibrin or fibrinogen. The obstruction can be, for example, an occlusive thrombus or a non-occlusive thrombus. Irradiation of the vessel wall in the vicinity of a thrombus leads to expansion of the thrombus with penetration into the thrombus of intrinsic chemical factors and, in some embodiments, extrinsic chemical factors which facilitate the release of individual thrombocytes. Accordingly, dissolution of a thrombus by a method of the invention is herein referred to as "dethrombosis". Thrombolysis, by contrast, is a process which releases clumps of thrombotic material, including platelet and erythrocyte aggregates, that originally were bound by fibrin strands which were dissolved by a lytic agent.

An intravascular thrombus which substantially occludes or partially occludes a blood vessel can be dissolved by directing a UV laser beam onto the wall of the blood vessel. The vessel is irradiated within about 1, 2, 3, 4, 5, 6, 7, 8, 9, 10, 12, 14, 16, 18, 20, 25, or 30 vessel diameters of the thrombus, wherein the vessel diameter referred to is determined as the average outer diameter over the occluded segment of a vessel. As used herein, the term "vessel diameter" refers to the outer diameter of a blood vessel. Preferably, the vessel is irradiated within about 10 vessel diameters of the thrombus. More preferably, the vessel is irradiated between about 1 and 4 vessel diameters removed from the thrombus. The vessel is preferably irradiated proximal to the thrombus. However, the vessel may be irradiated distal to the thrombus, in order to potentiate the removal of thrombotic material formed in the column of stagnated blood. Irradiation distal to the thrombus should be at a lower intensity than irradiation proximal to the thrombus, owing to the inability of the stagnated blood column to dissipate heat. A thrombus in a branch artery can also be dissolved by proximally irradiating the trunk artery at a distance of about 3, 4, 5, 6, 7, 8, 9, 10, 12, 14, 16, 18, 20, 25, or 30 vessel diameters from the thrombus. That is because the UV-induced vasodilation effect can propagate proximally as well as distally in a trunk artery and into branch arteries for a considerable distance of up to at least 20–30 vessel diameters. This phenomenon can be especially useful in cases where a surgeon does not have feasible access to a branch artery containing a thrombus but does have proximal access to the trunk artery.

In some embodiments of the method, the laser beam does not impinge on the thrombus itself; in other embodiments, the beam does impinge on the thrombus. Preferably, the beam is directed either onto the outer surface of the vessel using the beam emitted directly from the laser (if necessary, suitably conditioned by optical elements such as lenses or mirrors), or onto the inner surface by a beam transmitted through an optical fiber or liquid-core optical guide placed inside the vessel. In some embodiments, the laser beam does not impinge on the thrombosed vessel segment; in other embodiments, the beam can impinge on the thrombosed vessel segment.

Subsequent to irradiation with the laser beam, the vessel dilates first at the irradiated portion and then further continuously in the proximal and distal directions. When the dilation effect reaches the thrombosed segment, the thrombus itself dilates, which allows the infusion of blood together with intrinsic chemical substances, normally present in the body, which promote the dissolution or lysis of the thrombus. Optionally, extrinsic chemical substances (i.e., pharmacological agents) which promote the dissolution or lysis of the thrombus can be administered to the mammal in conjunction with the irradiation of the vessel or the thrombus. Any agent which promotes the dissolution of a thrombus (dethrombosis), lysis of a thrombus (thrombolysis), or which inhibits the reformation of a thrombus by platelet inhibition can be used in the invention. Three particularly useful types of pharmacological agents are dethrombosing agents, thrombolytic agents, and platelet inhibitors. Dilation of the vessel induces the thrombus to dissolve with little or no emission of emboli detectable by light microscopy. In some embodiments, the dissolution of the thrombus is chemically promoted by the presence of either intrinsic or extrinsic agents.

Laser beams used to treat occluded vessels can be either continuous or pulsed. Use of a pulsed laser reduces heat buildup and consequent damage in the target and surrounding tissues. If a pulsed laser is used, the pulse rate can be any rate consistent with delivery of an appropriate time-averaged intensity of irradiation to the target tissue, while avoiding individual pulses of such high intensity that lasting damage, i.e., damage which is irreversible in a physiologically relevant time frame (e.g., a period of hours to weeks), results in the target tissue. A laser which emits light in the UV range is used in order to produce the vasodilation effect (Morimoto et al., 1998). The UV light is preferably in the range of 180–400 nm in wavelength. More preferably the UV light is in the range of 300–400 nm. Even more preferably the UV light is about 340–380 nm, and most preferably it is about 350–360 nm. A frequency-tripled Nd:YAG laser emitting radiation of 355 nm is especially preferred. Other UV lasers which can be used with the invention include the XeCl eximer laser (308 nm), XeF laser (351 nm), ArF laser (193 nm), the KrF laser (248 nm), argon ion (334, 351, 364 nm), HeCd (325 nm), krypton ion (337, 351, 356 nm), nitrogen (337 nm), frequency-doubled tunable Ti:sapphire laser (350–400 nm), and the frequency doubled tunable alexandrite laser (360–400 nm). Any diode laser or dye laser can also be used provided that an output can be obtained in the UW range required for the vasodilation effect. In principle, any laser can be used which emits UW radiation either directly or as the result of frequency doubling or tripling.

A UV laser beam used in the invention can be applied to either an external or internal surface of an occluded vessel or to a thrombus in any desired manner. For example, the laser beam can be directly applied to the target by aiming the laser itself or through the use of one or more mirrors or lenses. The laser beam can also be directed onto its target using an optical fiber or optical guide. UV light penetrates biological tissues and blood rather poorly, to a depth of only about 30–50 µm. Any desired approach can be used which achieves adequate irradiation intensity of the target. For example, there can be direct contact between the output of the laser beam, e.g., a catheter containing an optical fiber or a liquid-core optical guide, and the target (i.e., the vessel wall or thrombus). Alternatively, blood can be temporarily flushed out of the path of the laser beam so that it can reach the target. Blood can be cleared from the path of the laser beam, for example, by flushing a small amount of physiological saline solution through the opening of the catheter from which the beam exits immediately prior to illuminating the vessel wall or thrombus (see Gal et al. 1992 and U.S. Pat. No. 5,649,923, incorporated herein by reference; also cf. FIG. 7).

The intensity of UV illumination is preferably adjusted so as to provide the minimal dose required to achieve the desired extent of vasodilation within the desired timeframe. For example, using a frequency tripled Nd-YAG laser, an incident intensity of about 5 watts/cm$^2$ produces a moderate, reversible dilation. Effective thrombus dilation and eventual dissolution can be achieved when the vessel diameter increases by approximately 20–40%, typically corresponding to a range of incident intensity of about 5 to about 10 watts/cm$^2$. However, excessively high intensities, e.g., greater than 20 watts/cm$^2$ (equivalent to an energy fluence of about 1 J/cm$^2$ per pulse at a pulse rate of 20 Hz) can produce a larger 80–100% increase in vessel diameter but may alter the vascular wall (small vacuoles are formed in the smooth muscle tissue), resulting in physiologically irreversible dilation (e.g., not reversed in some experiments after three days). Therefore, illumination intensity is preferably not greater than about 20 watts/cm$^2$. Nonetheless, an illumination intensity of about 20 watts/cm$^2$ does not cause vessel perforation. Vessel integrity is generally not compromised even at somewhat higher intensities because smooth muscle cells can be replaced naturally. In principle any degree of vessel dilation can be induced which achieves sufficient distension of the thrombus so as to cause it to dissolve. The intensities described in this paragraph are time-averaged incident intensities. For pulsed irradiation, the time-averaged intensity is used; therefore, for some protocols involving brief, intermittent pulses, higher intensities or energy fluences per pulse than those reported here could be used. Increases in vasodilation comparable to those reported here have been reported by others with similar energy fluences: Morimoto et al. (1998) used 0.8–2 mJ/mm$^2$/pulse of 248 nm KrF laser irrradiation on rat femoral arteries in vivo. In the visible region, Schwengel et al. (1993) used 577 nm pulsed dye laser irradiation at 25 mJ/mm$^2$/pulse to obtain a similar percentage of dilation in rabbit femoral artery, while Kaoutzanis et al. (1995) verified the phenomenon of visible laser-induced vasodilation but did not specify the energy fluence required. In these works the presence of hemoglobin or other colored material was required to observe dilation, while the ultraviolet technique does not (Furchgott et al., 1961; Chaudry et al., 1993).

Although the irradiation intensity guidelines provided above are generally believed to be applicable to all mammals, differences may arise due to the species of mammal, the size of the vessel, the composition of the vessel wall (e.g., the presence or absence of atheroma tissue), the mode of irradiation (e.g., whether pulsed or continuous), or other factors. Therefore, optimal performance of the method may require that the user adjust the incident intensities suggested above. A general approach to adjusting the incident intensity of the UV laser beam is as follows. The user should begin at a low intensity, e.g., an average intensity of about 1 watt/cm$^2$, or a lower intensity if required, which does not dilate the vessel if applied for about one minute. The incident intensity can then be increased in increments (e.g., increments of 1 or 2 watts/cm$^2$ or larger) until dilation of the vessel is observed within a reasonable time, e.g., within 30 seconds, 1 minute, 2 minutes, 5 minutes, 10 minutes, or longer). The period of irradiation can be continuous, i.e., lasting until the dilation effect plateaus, or can be intermittent, in which case the duration of one or more periods of irradiation can also be varied at a given incident intensity in order to obtain an appropriate response. The appropriate vasodilation response, i.e., extent of dilation and its kinetics of onset and duration, can be determined by the user; however, responses in the range of 20–40% increase in vessel diameter over 1–5 minutes would generally regarded by many users as appropriate (see, e.g., FIG. 3).

A pharmacological agent which aids in thrombus dissolution can be administered to the mammal receiving laser treatment. Any method which results in stretching or distension of the thrombus enhances the penetration into the thrombus of lytic agents and endogenous plasma factors such as antithrombin III or heparin cofactor-II (Callas and Fareed, 1995) and thereby accelerates recanalization of the occluded vessel. The use of both UV laser irradiation and a pharmacological agent which aids in thrombus dissolution can be synergistic, with the effects of UV irradiation disorganizing the thrombus by distension, thus allowing the penetration of intrinsic or extrisic pharmacological agents which can further augment the disruption or inhibition of chemical interactions that hold the thrombus together. While not wanting to limit the invention to any particular mechanism, it is possible that one effect of UV irradiation is to facilitate secretion or production of substances which activate endogenous dethrombosing or lytic pathways. Further benefits of combined UV radiation and pharmacological therapy are increased efficacy of the pharmacological agent, reduced dosage required for the pharmacological agent, extension of the time window for the treatment to be effective, and consequently fewer side effects from the pharmacological agent. In particular, the hemorrhagic complications of therapy with t-PA or other chemical agents, including dethrombosing, thrombolytic, antiplatelet, or neuroprotective agents (e.g., antiischemic agents, calcium channel blockers, NMDA antagonists, AMPA, or free radical scavengers), that prevent or reverse thrombosis, coagulation, platelet binding, or ischemic damage downstream from the vascular obstruction may be avoided by means of UV laser treatment combined with the chemical agent at lower doses than would be required without UV laser treatment.

Another important benefit of combining UV laser irradiation treatment with the use of pharmacological agents is that a more rapid dissolution of a thrombus can be achieved compared with either method alone. It is well known that rapid administration of t-PA, e.g., within 3 hours of the onset of acute ischemic stroke, improves clinical outcome (Marler et al., 1995). Therefore, the rapid dethrombosis achieved with UV laser irradiation therapy, especially when combined with pharmacological agents such as t-PA, platelet inhibitors ("platelet inhibitors" and "antiplatelet agents" refer herein to any substance which blocks a receptor-mediated pathway leading to platelet-platelet binding, aggregation, or adhesion to another membranous surface), or thrombin inhibitors, offers the potential for greatly improved therapeutic results.

The pharmacological agent can be administered prior to, during, or following the UV illumination. The agent should be administered within such a time period that it retains its effectiveness at the time the vessel is induced to dilate by UV laser irradiation. Preferably, the agent is administered prior to the laser irradiation. For example, the pharmacological agent can be administered no more than 1, 2, 3, 5, 7, 10, 15, 20, 30, 45, 60, 90, or 120 minutes prior to the laser irradiation. It can be administered by any route which is safe and efficacious for the agent, e.g., orally, intravenously, or intraarterially upstream from the thrombus. The pharmacological agent can also be administered through the same catheter which delivers the laser beam or another catheter at or near the location of the thrombus.

Suitable pharmacological agents include ones with thrombolytic, dethrombosing, or antiplatelet properties. Thrombolytic agents, such as tissue plasminogen activator (t-PA; any recombinant variant of t-PA can also be used, such as Activase® or Tenecteplase (TNKase™), urokinase, and streptokinase disrupt the fibrin filaments that hold together fibrin-containing thrombi. Dethrombosing agents act to dissociate aggregated platelets which are part of any thrombus. Dethrombosing agents include natural thrombin inhibitors such as heparin-antithrombin III complex, tick anticoagulant protein, hirudin (a highly specific thrombin inhibitor derived from the *Hirudo medicinalis* leech), and its recombinant varieties such as lepirudan ([Leu$^1$,Thr$^2$]-desulfohirudin, currently marketed as Refludan™) and the peptide hirulog. Thrombin inhibitors can dissociate thrombi because thrombin activity is required to maintain thrombus integrity (Mruk et al., 1996; Wysokinski et al. 1996). Synthesized small molecule thrombin inhibitors such as argatroban and inogatroban (Finkle et al., 1998) can also be used. Antiplatelet agents include RGD peptides which inhibit the formation of new GPIIIa-IIb complexes on dissociated platelets. The use of pharmacological agents in the invention is not limited to any particular agent or selection of agents; any pharmacological agent which aids in thrombus dissolution by either direct interference with preservation of intraplatelet bonding or by prevention of such bonding is suitable for use with the invention.

Any type of thrombus which occludes a blood vessel in a mammal can be dissolved by one or more of the methods of the invention. Thrombi can be generally classified into (1) substantially pure platelet thrombi, (2) thrombi composed predominantly of platelets and fibrin, and (3) thrombi comprising platelets, fibrin, red blood cells and minor amounts of other blood components. Some thrombi, such as pure platelet thrombi, are substantially free of fibrin. Thrombi which form in regions of high flow disturbance, e.g., areas of stenosis or branching, are more likely to be platelet-rich thrombi because these conditions favor platelet deposition (Chesebro and Fuster, 1991). Stasis, on the other hand, favors fibrin formation. Fibrin-free or fibrin-poor thrombi are resistant to thrombolytic agents (e.g., t-PA) and are very difficult to dissolve reliably and quickly using available techniques. However, the UV irradiation method of the current invention has proven highly effective at dissolving such thrombi (see Example 3). The methods of the invention can be used to aid in the dissolution of both occlusive thrombi (i.e., thrombi which block substantially all of the blood flow through past the occluded segment) and partially occlusive or non-occlusive thrombi (thrombi which block less than substantially all of the blood flow past the occluded segment).

The methods of the present invention are suitable for treating a variety of disease conditions which involve occlusion of a blood vessel. Examples of such conditions include stroke, myocardial infarction, and occlusion of any artery or vein, large or small. Large vessels can be treated using either irradiation from within the vessel, via catheterization, or irradiation of the external surface of the vessel. Vessels which are too small for effective catheterization, for example intraocular arteries, can be irradiated on their external surfaces. Prior to irradiation of an occluded vessel, the position of the thrombus responsible for the occlusion can be determined by any method known in the art. Suitable techniques include, for example, obtaining an arteriogram after introducing X-ray contrast fluid into the artery or vein upstream of the thrombus or analogous methods using magnetic resonance imaging (MRI).

Irradiation of the luminal surface of a vessel requires introduction of the laser beam through an optical fiber or other optical guide inserted into a catheter or used as a catheter. In order to symmetrically illuminate the vessel wall and not the thrombus itself, a ring-shaped laser beam can be obtained from an optical fiber or liquid core optical guide by introducing an ordinary gaussian laser beam into the proximal end of the fiber or guide at an angle to the central axis of the fiber. The angle of incidence at which the laser beam is introduced into the fiber can be in the range from about 1, 2, 3, 4, 5, 6, 7, 8, 9, or 10 degrees to about 10, 12, 14, 15, 16, 18, 20, 22, 25, 30, 35, or 40 degrees with respect to the central axis of the fiber. Preferably the angle of incidence is between about 5 and about 20 degrees, although any angle from 1 to 30 degrees is usable. However, if the angle of incidence exceeds that angle specified by the numerical aperture (N. A.) of the optical fiber, the fidelity of laser power transmission is lessened, owing to conduction of light through the fiber cladding layer. For a 0.22 N. A. fiber, the maximum angle of incidence for optimum light conduction is 12.7 degrees. By adjusting the angle of incidence, it is possible to adjust the thickness of the ring beam and therefore to adjust the incident intensity of the UV radiation and to compensate for differences in vessel diameter, so that a ring beam of desired position and intensity is obtained. Variation of the angle of incidence will determine the thickness of the ring beam produced at the distal end of the fiber, and therefore directly affects the illumination intensity at the vessel wall. The relationship between the angle of incidence at the proximal end of the fiber and the position and intensity of the ring beam is developed in further detail in Example 5.

A ring output beam may be obtained by at least two other methods. In the following two cases, the direction of the incident beam is collinear with the axis of the optical fiber; thus the entire surface area of the fiber is available to accept the incident beam. This represents an important advantage when compared to the geometry of FIG. 7, in which the surface area available for beam introduction is reduced by the cosine of the angle of incidence. In the first case, a conical lens with apex angle "alpha" is used to focus the beam onto the fiber at perpendicular incidence. The conical lens is collinear with the axis of the beam and the axis of the fiber and can either be external to the fiber or attached to the end of the fiber. A cone of light (which will project onto a perpendicular surface as a ring beam) will emerge from the output end, subtending a full angle equal to the complement (180 degrees—alpha) of the apex angle of the lens. Alternatively, a ring beam may be obtained by introducing the beam collinearly into an optical fiber whose face is beveled at an angle $\theta_B$. In this case of collinear incidence, the light path inside the fiber will be exactly the same as that for angled incidence onto a flat-faced fiber (as in FIG. 7), but the exit angle in air $\theta_{out}$ will be related to $\theta_B$ by $\theta_{out}=(n-1)(\theta_{out}$, where we have used the small angle approximation.

UV laser light can be aimed directly onto a thrombus, preferably by the intraarterial route. The energy fluence (mJ/mm$^2$ or J/cm$^2$ per pulse) range of the pulsed laser incident illumination to be used with the methods of the invention (i.e., "low energy fluence" irradiation) is considerably (10–100 times) below those which have been used thus far for thrombus removal by direct irradiation. The high energy fluences used with previously available methods produce either photoacoustic (shock wave) effects, or instantaneous vaporization of the thrombus. The photoacoustic effects lead to the formation of gas bubbles under high pressure, inducing tissue disintegration below the vaporization threshold (i.e, inertially confined ablation). Above that threshold, with a laser of yet higher energy fluence, sudden and essentially complete vaporization of a thrombus (i.e., instantaneous ablation) has been achieved with previous methods. However, using a frequency-tripled Nd:YAG laser at 355 nm according to this invention at an intensity up to about 20 watts/cm$^2$ (i.e., equivalent to energy fluences of up to about 1 J/cm$^2$ per pulse at a pulse rate of 20 Hz) does not produce photoacoustic or instantaneous ablation effects; the invention therefore does not facilitate "debulking" of the thrombus. While applicant does not wish to be bound by any particular theory of operation, it is believed that such low intensity illumination causes a soluble vasorelaxant factor to be released from either vascular smooth muscle cells or platelets, resulting in vasodilation and thrombus dissolution either separately or simultaneously. Direct UV illumination of the thrombus can optionally be combined with UV illumination of the vessel wall and/or the administration of a pharmaceutical agent which aids in thrombus dissolution, as described above.

The above disclosure generally describes the present invention. A more complete understanding can be obtained by reference to the following specific examples, which are provided herein for purposes of illustration only and are not intended to limit the scope of the invention.

EXAMPLE 1

Figure 1:
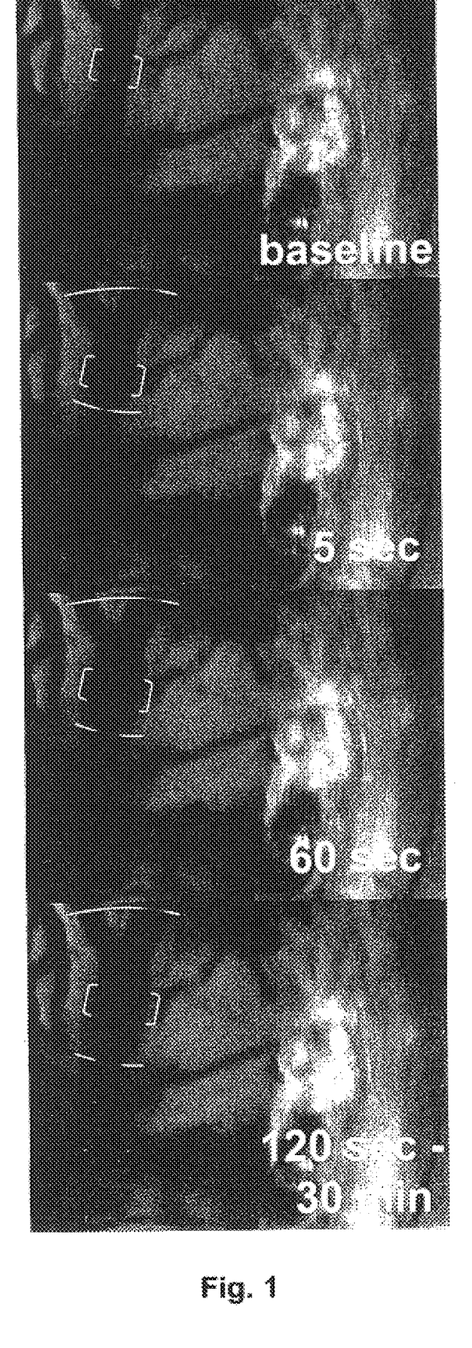
FIG. 1 demonstrate the spreading and time course of the dilation induced in a rat dorsal middle cerebral artery by UV Nd:YAG laser irradiation at a wavelength of 355 nm and an intensity of 5 watts/cm$^2$.
Figure 2:
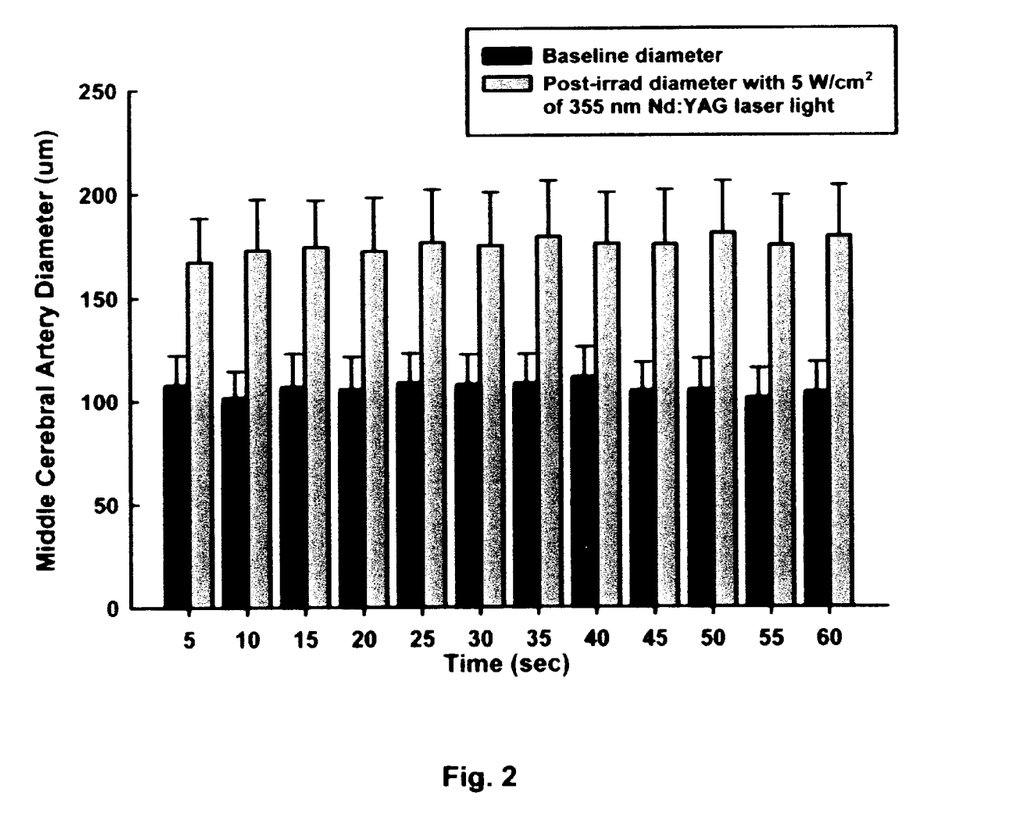
FIG. 2 shows the response of a representative middle cerebral artery segment following irradiation at 5 watts/cm$^2$ of UV laser light for a period of two minutes.
Figure 3:
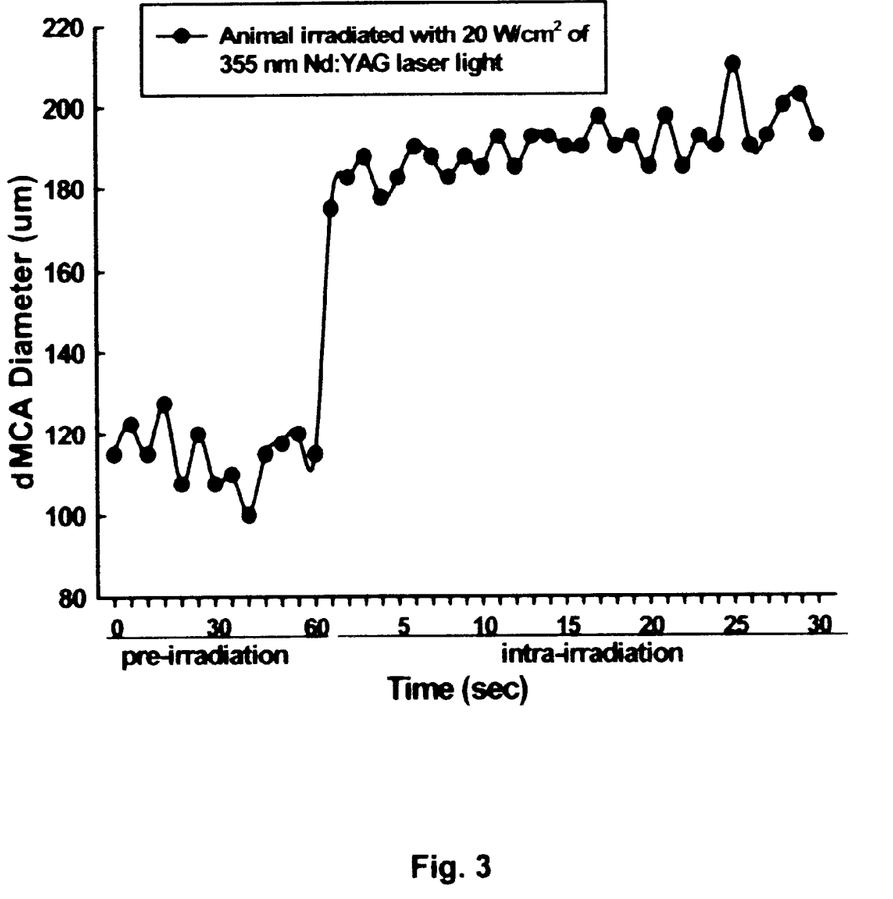
FIG. 3 illustrates the rapid onset of vasodilation in a middle cerebral artery irradiated at 20 watts/cm$^2$ of UV laser light. Vascular diameter stabilizes within 30 sec of irradiation.

Vasodilatory Response in the Rat Distal Middle Cerebral Artery to UV Laser Light In six rats, a closed cranial window made of fused silica was created over the distribution of the dorsal middle cerebral artery to facilitate undistorted visualization and measurement of vascular diameters. A Q-switched Nd:YAG laser operating at 20 pulses per second (5 nanosecond pulse duration) and at a frequency-tripled UV wavelength of 355 nm was used as the irradiation source. The response of a representative arterial segment irradiated with 5 watts/cm$^2$ of UV laser light for a period of two minutes is shown in FIG. 1. The vessel dilated quickly and remained dilated up to 30 min after irradiation. Irradiation with an average intensity of 5 watts/cm$^2$ of UV laser light facilitated a dilation of 62.2±7.8 % with respect to baseline (FIG. 2). Dilations were almost instantaneous (<1 sec within the start of irradiation) and reached their maximum within 5 sec (FIG. 3). The percent increase in dorsal middle cerebral artery diameter following irradiation was independent of vessel size. Pre-irradiation diameters of the arterial blood columns ranged from 36.2 to 164 $\mu$m. The normalized change in column diameter between systole and diastole (a measure of wall elasticity) for pre- and post irradiation conditions was 6.4 and 5.9 %, respectively, suggesting the absence of functional damage to the vessel wall owing to the preservation of compliance (van Bortel et al., 1995). Electron microscopic analysis of two rats irradiated with an intensity of either 5 or 20 watts/cm$^2$ revealed normal-appearing intimal and medial vascular morphology indistinguishable from control vessels for the lower power setting. At the higher power setting, there was evidence of smooth muscle swelling confined to the irradiated segment. The dilation persisted for at least several hours with irradiation at 20 watts/cm$^2$, whereas at 5 watts/cm$^2$ it began to return to normal after 60–90 minutes.

EXAMPLE 2

Pure Platelet Thrombus

Figure 4:
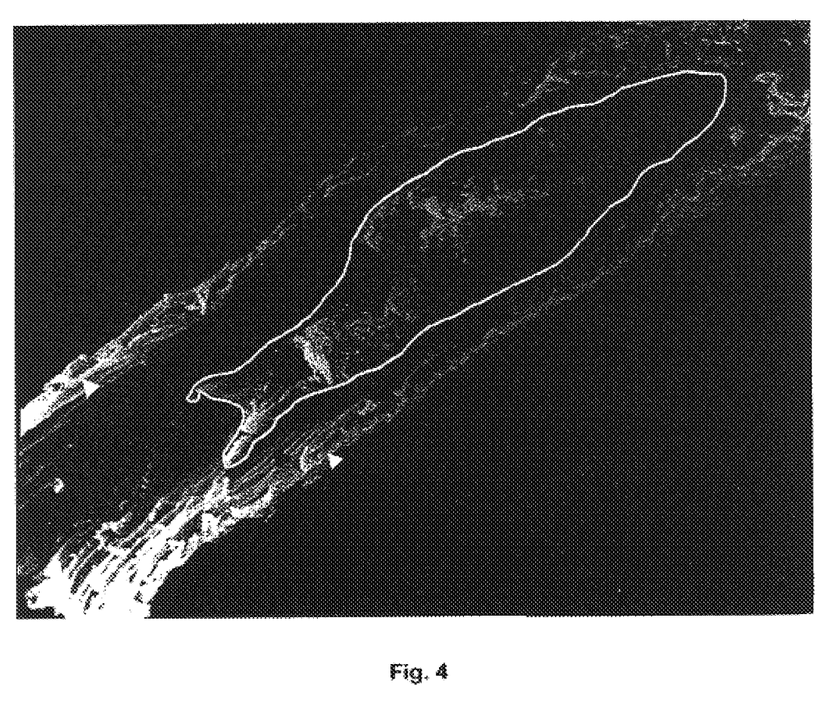
FIG. 4 displays a scanning electron micrograph of a longitudinal section of a photothrombotically occluded middle cerebral artery of a rat. A large white thrombus, apparently consisting entirely of platelets, occludes the vessel entirely. Vasoconstriction is demonstrated by the lengthwise corrugations proximal and distal to the thrombus.

FIG. 4 shows an electron micrograph of a pure platelet thombus occluding a rat middle cerebral artery. The thrombus was produced in vivo using an intravascular photochemical reaction, sensitized by the interaction of a greenish-yellow laser beam with the organic dye rose bengal, as described in U.S. Pat. No. 5,053,006, incorporated herein by reference (Watson, 1991; also cf. Watson et al., 1995). This thrombus was generated as a natural response to endothelial damage sensitized by the dye-laser light interaction (in contrast to the usual method of ex vivo formation and injection into the subject artery). Pure platelet thrombi are stabilized not by fibrin, but by intraplatelet fibrinogen cross links between GPIIb-IIIa platelet membrane receptors. Owing to the lack of fibrin, this type of thrombus is insensitive to treatment with t-PA.

EXAMPLE 3
UV laser-facilitated Dissolution of a Pure Platelet Thrombus.

Figure 5:
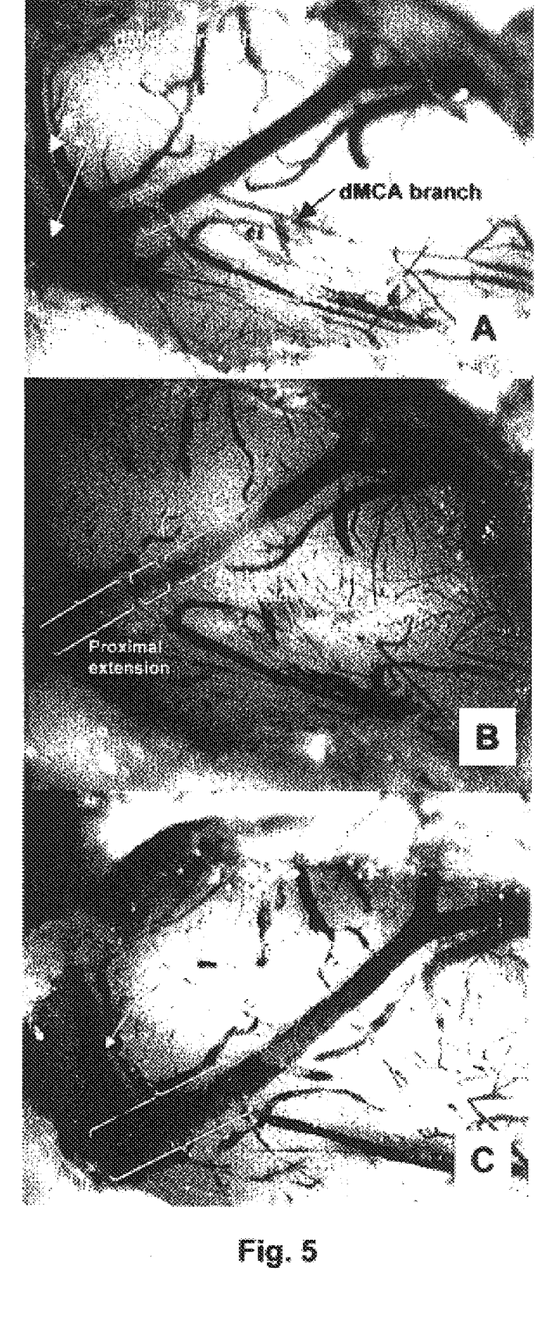
FIGS. 5A–C show a distal middle cerebral artery segment in a rat before (A) and after (B) rose bengal dye-mediated photothrombotic occlusion yielding a pure platelet thrombus, and after treatment with up to 5 watts/cm$^2$ with 355 nm Nd:YAG laser irradiation. Note the establishment of reflow (C).

This experiment was initially designed to determine whether UV laser-induced dilation of the thrombosed distal middle cerebral artery would allow the vascular wall to expand beyond the thrombus dimensions and provide pathways for blood to bypass the thrombus (Nakayama et al., 1988). Accordingly, the distal middle cerebral artery of a rat was occluded with a single photothrombus (cf. Example 2 and FIG. 5B) and irradiated at sites proximal to the thrombus with the 355 nm Nd:YAG laser at intensities of ca. 1–5 watts/cm². The occluded segment responded in an entirely unanticipated fashion: no separation between the vessel wall and thrombus was seen. Instead the thrombus expanded congruently with the arterial segment, and was very soon penetrated by tiny rivulets of blood, which increased in diameter and flow conduction volume (see the appearance at 30 min, FIG. 5C) until the entire thrombus was eventually washed away by the blood stream. When a thrombus is dilated in this fashion its density decreases, presumably allowing penetration of plasma factors with thrombolytic or dethrombosing capability. The process is complete within 20 minutes for thrombi aged less than 30 minutes; more time is required to establish reflow as the platelet thrombus ages, owing to downstream coagulation of stagnant blood. When lysis is complete, a thin layer of platelets remains behind. These platelets had initially adhered to the photochemically damaged endothelium and then degranulated, thereby sensitizing the formation of the occlusive platelet mass. The recanalized artery otherwise appeared normal.

Similar results were obtained even if UV irradiation was initiated 2–3 hours after photochemical occlusion of the middle cerebral artery. In all cases, no embolus emission was observed upon dissolution of the thrombus. Apparently, the reduced density of the dilated thrombus permitted penetration of circulating "dethrombosis" factors (Wysokinski et al., 1996) such as antithrombin III or heparin cofactor-II (Callas and Fareed, 1995), resulting in disaggregation and presumably release of individual platelets.

EXAMPLE 4
UV-induced Dissolution of a Fibrin-containing Thrombus

Figure 6:
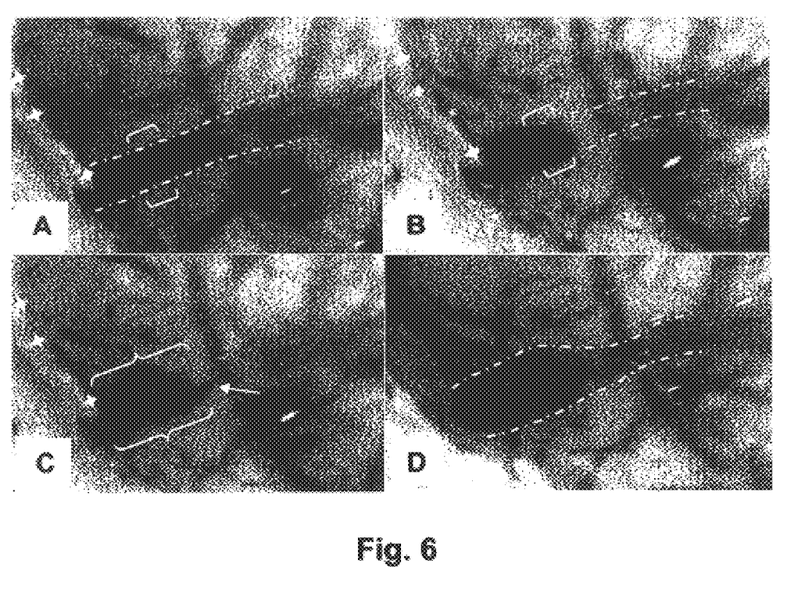
FIGS. 6A and 6B show a middle cerebral artery segment before (A) and after (B) occlusion with a fibrin-stabilized red thrombus, formed by the interaction of intravenously injected flavin mononucleotide and a 457.9 nm argon laser beam (brackets indicate position of irradiation).
FIGS. 6C and 6D show the results of UV Nd:YAG laser treatment at up to 5 watts/cm$^2$ for two time points (C, 30 min and D, 60 min) postocclusion. Note that reflow is obtained without addition of tissue plasminogen activator.

FIGS. 6A and B shows a rat middle cerebral artery before (A) and after (B) production of an occlusive fibrin-stabilized red thrombus. The brackets show the location of the thrombus, which was red in color. The thrombus was produced by an intravascular Type I (free radical-mediated) photochemical reaction, sensitized by the interaction of the 457.9 nm deep blue argon laser transition with the photosensitizing agent, flavin mononucleotide (FMN) (cf., Watson et al., 1995). The laser irradiation was administered for 4 minutes at a focussed intensity of ca. 21 watts/cm² and a concentration of FMN in blood of 1.3 mM. The thrombus was allowed to stabilize for 1 hour. FIGS. 6C and D shows the results of UV laser irradiation of the external surface of the proximal arterial segment (not visible at the beginning of treatment). With 355 nm Nd:YAG treatment administered at intensities of up to 5 watts/cm², reflow was apparent at 30 min (C, arrow) and was more prominent at 60 min (D). In this case the artery was partially dilated due to the bulk of the photochemically generated fibrin-stabilized red thrombus. Nevertheless, UV laser treatment caused further dilation and successfully dissolved the thrombus without the administration of t-PA.

Figure 7:
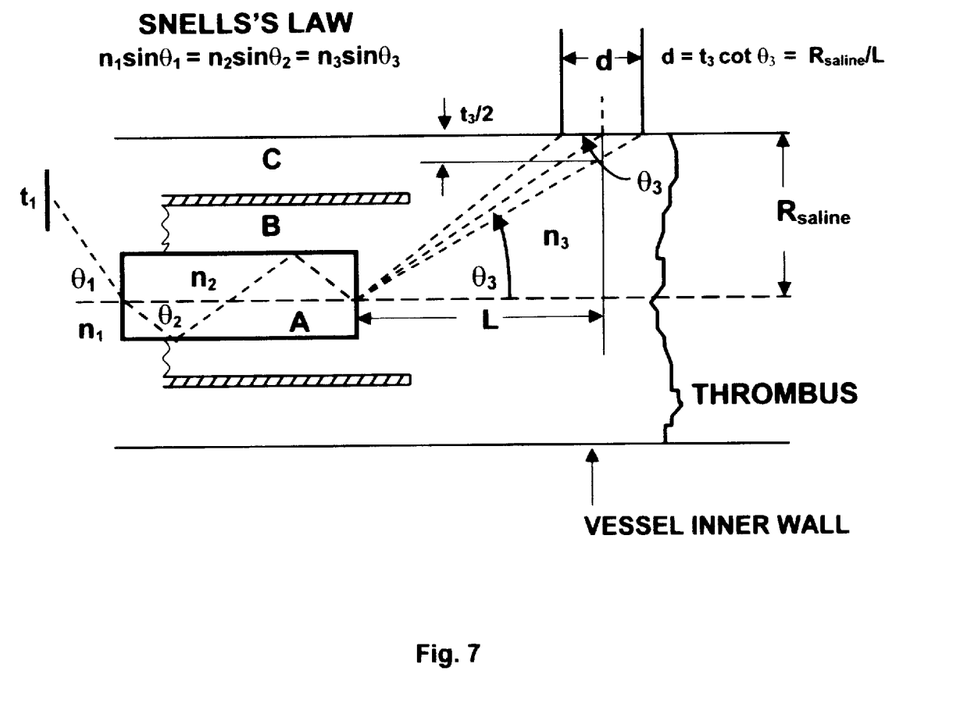
FIG. 7 presents the geometry of the introduction of a laser beam into a catheterized optical fiber at a non-zero angle of incidence. This results in the production of an output beam in the shape of a ring circumscribing the axis of the fiber, and the consequent ring beam projects circumferentially onto the inner wall of a blood vessel.

EXAMPLE 5
Production of a Ring Beam for Lumenal Irradiation of a Blood Vessel A ring-shaped beam of laser light is desirable for the irradiation of the lumenal surface of a blood vessel, in order to initiate vasodilation. Ring beams suitable for this task were produced by introducing an ordinary gaussian laser beam into a fused silica optical fiber at an angle of incidence to the axis of the fiber of between 5 and 35 degrees. The angle of incidence is indicated in FIG. 7 as $\theta_1$. In practice, incidence angles greater than that permitted by the numerical aperture (N.A.) of the optical fiber are seldom used owing to increasing loss of light from the core to the cladding, where it is absorbed or transmitted away, but if the fiber is rather short (a few meters), useful power may be obtained even for angles exceeding the N.A. criterion. For a fiber with an N.A. of 0.22, the maximum incidence angle (limit of no cladding losses) is 12.7 degrees.

The thickness of the ring beam on the interior surface of the vessel wall, d, is determined by adjusting the angle of incidence, $\theta_1$, for the radius of the blood vessel, R, at a working distance, L. The relationships among these variables are demonstrated in Table 1 based on measurements obtained using an argon laser operating at 514.5 nm focussed into a fused silica optical fiber with a core diameter of 400 μm and length of 2 meters. Table 1 contains direct measurements in mm of the ring beam radius and thickness at a constant distance (100 mm) from the optical fiber (n=1.45) as a function of the exit angle in air (n=1). This assessment must be done again if the optical fiber if any relevant characteristic (core diameter, composition, length) of the optical fiber is changed. In this initial example, the exit angle equals the angle of incidence. It is readily apparent that the beam thickness t, decreases as the exit angle increases.

The remainder of Table 1 tabulates the incidence and exit angles as the beam travels from the air through the fiber and then into a blood vessel temporarily filled with saline solution (n=1.33). The purpose of Table 1 is to calculate by Snell's Law the exit angle $\theta_3$ from a given incidence angle $\theta_1$, which then enables calculation of the horizontal projection, d, of the beam thickness on the arterial wall. This parameter d will stipulate how close the optical fiber can approach the thrombus in order to irradiate the inner arterial wall with a beam of thickness d without impinging on the thrombus. The function of the table is thus to reveal the relationships among the angles of incidence and exit as the ring beam dimensions are transformed by the beam's passage through the different media. All measurements of length in the table serve only to generate the incidence and exit angles, and thus need not be specified directly for an actual vessel (see the following discussion).

In FIG. 7, the horizontal projection d is shown to arise from the spread in exit angle $\theta_3$ (arising from the properties of the ring beam). Because the exit angle, as well as its spread, is a function of the refractive index of the medium, the beam thickness data must also be transformed appropriately for the medium in which the beam projects. Fortuitously, the exit angle spread decreases as the exit angle increases. This has the effect of equalizing the projections d/2 to the left and right of the line defined by the distance L. Therefore, by alternating interior angles, $$d = t_3 \times \text{cotangent}(\theta_3). \tag{1}$$

The beam half-thickness $t_3/2$ in the medium $n_3$ (referring to the geometry of FIG. 7) is derived as a consequence of Snell's law:

$$t_3/2 = t_1/2 \times \sin(\theta_3)/\sin(\theta_1) = t_1/2 \times n_1/n_3 \quad (2)$$

Table 1 can be used to calculate L, the distance of the optical fiber from the center of the ring beam projected on the vessel wall ("working distance") for a given irradiation condition. First, note that the ring beam radius observed in air (column at left) will be changed in saline solution, just as its thickness $t_3$ was in formula (2); the column "$R_{saline}$" is the result. The following example illustrates how to calculate the working distance, L, in order to irradiate the inside of an artery with a projected beam thickness $d = R_{saline}$. This specific parameters for which d is chosen to be equal to the vessel radius are not directly given in Table 1, but should occur between $R_{saline} = 11.65$ to 16.16 and the projection $d = 22.69$ to 11.75. (Since this discussion is concerned with calculating angles, the units of length are nonessential). By simultaneous interpolation, we derive that when $d = R_{saline} = 14.87$, this point is the same fractional distance (0.715) between the lower and upper values for $R_{saline}$ and d, respectively. Angle $\theta_3$ is then calculated by the same interpolation to be 8.38 degrees. By Snell's Law (see FIG. 7) $\theta_2 = 7.68$ degrees and the angle of incidence $\theta_1 = 11.18$ degrees.

For this example, the minimum distance from the optical fiber to the thrombus can be seen from FIG. 7 to be $$L_{min} = L + d/2, \quad (3)$$

where d/2 is either given in formula (1) or is defined by the clinician. Also note from FIG. 7 that $\cot(\theta_3) = L/R_{saline}$; thus $L = R_{saline}\cot(\theta_3)$. In this example, $L_{min}$ would equal $R_{saline}(\cot(\theta_3) + \frac{1}{2}) = 8.05 R_{saline}$.

To illustrate the use of Table 1, suppose the inner wall of the human middle cerebral artery, which has a nominal radius of 1.5 mm, is to be irradiated under the condition above ($d = R_{saline}$) To find $L_{min}$, substitute R=1.5 mm and $\theta_3 = 8.38$ degrees into the formula above for $L_{min}$ to get $L_{min} = 8.05 \times 1.5$ mm $= 12.08$ mm. The minimum volume of saline required to flush away the blood between the fiber tip and the thrombus is 12.08 mm×3.14×1.5 mm×1.5 mm=85.4 µl. The typical injection volume of contrast fluid into a middle cerebral artery is 1 ml, so the calculated displacement volume is well within clinical guidelines. The UV laser is pulsed during the period of the saline flush, resulting in arterial dilation. Increases in injection volume will thus be necessary as the artery dilates.

Ring beam thickness vertical projection $t_1$ in air, horizontal projection (d) on the vessel wall, and angles of incidence $\theta_1$ and exit $\theta_3$, as defined in FIG. 7, were determined using three different refractive media. All measurments were obtained for L =100 mm. See Example 5 for details.

TABLE 1

Ring beam thickness vertical projection $t_1$ in air, horizontal projection (d) on the vessel wall, and angles of incidence $\theta_1$ and exit $\theta_3$, as defined in FIG. 8, were determined using three different refractive media. All measurements were obtained for L = 100 mm. See Example 5 for details.

| $R_{air}$ | $t_1/2$ | $\theta_1$ | $\theta_2$ | $\theta_3$ | $R_{saline}$ | d/2 |
|---|---|---|---|---|---|---|
| 9.5 | 4 | 6.03 | 4.15 | 4.53 | 7.14 | 42.19 |
| 11 | 3.5 | 6.97 | 4.80 | 5.24 | 8.27 | 31.90 |
| 15.5 | 3.5 | 9.79 | 6.74 | 7.35 | 11.65 | 22.69 |
| 21.5 | 2.5 | 13.48 | 9.26 | 10.10 | 16.16 | 11.75 |

TABLE 1-continued

Ring beam thickness vertical projection $t_1$ in air, horizontal projection (d) on the vessel wall, and angles of incidence $\theta_1$ and exit $\theta_3$, as defined in FIG. 8, were determined using three different refractive media. All measurements were obtained for L = 100 mm. See Example 5 for details.

| $R_{air}$ | $t_1/2$ | $\theta_1$ | $\theta_2$ | $\theta_3$ | $R_{saline}$ | d/2 |
|---|---|---|---|---|---|---|
| 27.5 | 2.5 | 17.08 | 11.78 | 12.37 | 20.68 | 9.24 |
| 33.5 | 2.5 | 20.58 | 14.06 | 15.35 | 25.19 | 7.65 |
| 41 | 2 | 24.77 | 16.85 | 18.41 | 30.83 | 5.05 |
| 45 | 2 | 26.92 | 18.27 | 19.97 | 33.83 | 4.64 |
| 47 | 2 | 27.97 | 18.95 | 20.72 | 35.34 | 4.46 |
| 51.5 | 2 | 30.28 | 20.45 | 22.38 | 38.72 | 4.10 |
| 61.5 | 1.5 | 35.10 | 23.70 | 25.77 | 46.74 | 2.63 |

References

Buckley L A, Nesbit G M, Clark W M, Janis A D, Zeibol R, Gregory K W. Laser thrombolytic therapy for experimental cerebral thrombosis. Stroke 30:245, 1999 (abstract).

Callas D, Fareed J. Comparative pharmacology of site directed antithrombin agents. Implication in drug development. Thromb. Haemostasis 74:473–481, 1995.

Chaudry H, Lynch M, Schomacker K, Bimgruber R, Gregory K, Kochevar I. Relaxation of vascular smooth muscle induced by low-power laser irradiation. Photochem. Photochem. 58:661–669, 1993.

Chesebro J H, Fuster V. Dynamic thrombosis and thrombolysis: Role of antithrombins. Circulation 83:1815–17, 1991.

Davies M J, Thomas A C. Plaque fissuring: The cause of acute myocardial infarction, sudden ischemic death, and crescendo angina. Br. Heart J. 53:363–373, 1985.

del Zoppo G, Poeck K, Pessin M, et al. Recombinant tissue plasminogen activator in acute thrombotic and embolic stroke. Ann. Neurol. 32:78–86, 1992.

Fernandez-Ortiz A, Badimon J J, Falk E, Fuster V, Meyer B, Mailhas A, Weng D, Shah P K, Badimon L. Characterization of the relative thrombogenicity of atherosclerotic plaque components: implications for consequences of plaque rupture. J. Am. Coll. Cardiol. 23:1562–1569, 1994.

Finkle C D, St. Pierre A, Leblond L, Deschenes I, DiMaio J, Winocur P. BCH-2763, a novel potent parenteral thrombin inhibitor, is an effective antithrombotic agent in rodent models of arterial and venous thrombosis: Comparisons with heparin, r-hirudin, hirulog, inogatran, and argatroban. Throm. Haemost. 79:431–438, 1998.

Furchgott R F, Erreich S J, Greenblatt E. The photoactivated relaxation of smooth muscle of rabbit aorta. J. Gen. Physiol. 44:499–519.

Gal D, Chokshi S K, Mosseri M, Clarke R H, Isner J M. Percutaneous delivery of low-level laser energy reverses histamine-induced spasm in atherosclerotic Yucatan microswine. Circulation 85:756–768, 1992.

Kaoutzanis M C, Peterson J W, Anderson R R, McAuliffe D J, Sibilia R F, Zervas N T. Basic mechanism of in vitro pulsed dye-laser-induced vasodilation. J. Neurosurg. 82:256–261, 1995.

Litvak F, Eigler N, Margolis J, et al. Percutaneous excimer laser coronary angioplasty: Results in the first consecutive 3000 patients. J. Am. Coll. Cardiol. 23:323–329, 1994.

Marler J, et al. (National Institute of Neurological Disorders and Stroke rt-PA Stroke Study Group) Tissue plasminogen activator for acute ischemic stroke. New Eng. J. Med. 333:1581–87, 1995.

Morimoto Y, Arai T, Matsuo H, Kikuchi M. Possible mechanisms of vascular relaxation induced by pulsed-UV laser. Photochem. Photobiol. 68:388–393, 1988.

Mousa S A, Forsythe M S, Diemer M, Bozarth J M, Reilly T M. Thrombolytic and antithrombotic efficacy of he platelet GPIIb-IIIa antagonist DM728. Coronary Artery Disease 5:919–927, 1994.

Mruk J S, Zoldhelyi P, Webster M W I, Heras M, Grill D E, Holmes D R Jr, Fuster V, Chesebro J H. Does antithrombotic therapy influence residual thrombus after thrombolysis of platelet-rich thrombus? Circulation 93:792–799, 1996.

Nakayama H, Dietrich W D, Watson B D, Busto R, Ginsberg M D. Photothrombotic occlusion of rat middle cerebral artery: histopathological and hemodynamic sequelae of acute recanalization. J Cerebr Blood Flow Metab 8:357–366, 1988.

Schwengel R H, Gregory K W, Hearne S E, Scott H J, Beuman G J, Mergner W J, Caplin J L, Ziskind A A. Characterization of pulsed-dye laser-mediated vasodilatation in a rabbit femoral artery model of vasoconstriction. Lasers Surg, Med. 13:284–295, 1993.

Topaz O, McIvor M, Stone G, Foschi A, Sutko J, DeMarchena E. Holmium laser multicenter investigators: Solid state laser coronary angioplasty multicenter registry report. Circulation (suppl. 1):332, 1994.

Topaz O. Plaque removal and thrombus dissolution with the photoacoustic energy of pulsed-wave lasers: Biotissue interactions and their clinical manifestations. Cardiology 87:384–391, 1996.

Topaz O. Acute results, complications, and effect of lesion characteristics on outcome with the solid-state, pulsed-wave, mid-infrared laser angioplasty system: Final multicenter registry report. Lasers Surg. Med. 22:228–239, 1998.

van Bortel L M A B, Kool M J F, Spek J J. Disparate effects of antihypertensive drugs on large artery distensibility and compliance in hypertension. Am. J. Cardiol. 76:46E–49E, 1995.

Watson B D. Method for the Permanent Occlusion of Arteries. U.S. Pat. No. 5,053,006 awarded Oct. 1, 1991.

Watson B D, Dietrich W D, Prado R, Nakayama H. Kanemitsu H, Futrell N N, Yao H, Markgraf C G, Wester P: Concepts and techniques of experimental stroke induced by cerebrovascular photothrombosis. In Ohnishi S T, Ohnishi T (eds): Central Nervous System Trauma: Research Techniques. CRC Press, Boca Raton, FL, pp 169–194, 1995.

Wysokinski W, McBave R, Chesebro J H, Owen W G. Reversibility of platelet thrombosis in vivo. Quantitative analysis in porcine carotid arteries. Thromb. Hemostasis 76:1108–113, 1996.

What is claimed is:

1. A method for dissolving a thrombus in a blood vessel of a mammal, comprising the step of:
   directing an ultraviolet laser beam onto an external or internal surface of the blood vessel within about 20 vessel diameters of the thrombus but not impinging on the thrombus, wherein the laser beam does not produce a photoacoustic shock effect, wherein the vessel dilates during or following exposure to the laser beam, whereby the thrombus subsequently dissolves.

2. The method of claim 1, wherein the laser beam is directed onto the blood vessel between about 1 and about 4 vessel diameters removed from the thrombus.

3. The method of claim 1, wherein the laser beam is directed onto the vessel by transmission through an optical fiber.

4. The method of claim 1, wherein the laser beam is directed onto the vessel by transmission through a liquid core optical guide.

5. The method of claim 1, wherein the laser beam is continuous.

6. The method of claim 1, wherein the laser beam is pulsed.

7. The method of claim 1, wherein the laser emits light at a wavelength of about 180–400 nm.

8. The method of claim 7, wherein the laser emits light at a wavelength of about 300–400 nm.

9. The method of claim 8, wherein the laser is a frequency-tripled Nd:YAG laser which emits light at 355 nm.

10. The method of claim 1, wherein the incident intensity of the laser beam is between about 1 and about 20 watts per square centimeter.

11. The method of claim 1 further comprising the step of:
    administering to the mammal a pharmacological agent which aids in thrombus dissolution.

12. The method of claim 11, wherein the pharmacological agent is a thrombolytic agent.

13. The method of claim 12, wherein the thrombolytic agent is a fibrinolytic enzyme.

14. The method of claim 13, wherein the fibrinolytic enzyme is selected from the group consisting of tissue plasminogen activator, a recombinant variant of tissue plasminogen activator, uroliase, and streptokinase.

15. The method of claim 11, wherein the pharmacological agent is a dethrombosing agent.

16. The method of claim 15, wherein the dethrombosing agent is selected from the group consisting of hirudin, hirulog, lepirudan, heparin-antithrombin III complex, and argatroban.

17. The method of claim 11, wherein the pharmacological agent is a thrombin inhibitor.

18. The method of claim 11, wherein the pharmacological agent is an antiplatelet agent.

19. The method of claim 18, wherein the antiplatelet agent is an inhibitor of GPIIb-GPIIIa interaction.

20. The method of claim 18, wherein the antiplatelet agent is an inhibitor of fibrinogen-platelet interaction.

21. The method of claim 1, wherein the thrombus is a substantially pure platelet thrombus.

22. The method of claim 1, wherein the thrombus comprises both platelets and fibrin.

23. The method of claim 1, wherein the thrombus comprises platelets, fibrin, and red blood cells.

24. The method of claim 1, wherein the mammal has suffered a vessel occlusion.

25. The method of claim 24, wherein the vessel occlusion resulted in a stroke.

26. The method of claim 24, wherein the occluded vessel is an artery.

27. The method of claim 1, wherein the beam is directed to the internal surface of the vessel.

28. The method of claim 27, wherein the beam is introduced into an intravascular optical fiber or liquid core optical guide at an angle of incidence of between about 5 and 20 degrees from the central axis of the optical fiber.

29. The method of claim 27, wherein the beam is coupled into an intravascular optical fiber or liquid core optical guide by a conical lens.

30. The method of claim 1, wherein the beam is directed onto the external surface of the vessel.

31. The method of claim 1, wherein the thrombus is located in a branch artery and the laser beam is directed onto an internal or external surface of a corresponding trunk artery.

32. A method for dissolving a thrombus in a blood vessel of a mammal, comprising the step of:

directing an ultraviolet laser beam onto a thrombus in a blood vessel using an intravascular optical fiber or liquid core optical guide, wherein the laser beam does not instantaneously ablate or photoacoustically shock the thrombus, whereby the thrombus subsequently dissolves.

33. The method of claim 32, wherein the incident intensity of the laser beam is between about 1 and about 20 watts per square centimeter.

34. The method of claim 32, wherein the vessel dilates.

35. The method of claim 32 further comprising the step of:

administering to the mammal a pharmacological agent which aids in thrombus dissolution.

36. The method of claim 32, wherein the thrombus is a substantially pure platelet thrombus.

37. The method of claim 32, wherein the thrombus comprises both platelets and fibrin.

38. The method of claim 32, wherein the thrombus comprises platelets, fibrin, and red blood cells.

39. The method of claim 32, additionally comprising the step of:

directing the ultraviolet laser beam onto the blood vessel within about 20 vessel diameters of the thrombus, but not impinging on the thrombus.

40. The method of claim 39, wherein the ultraviolet laser beam is directed onto the blood vessel between about 1 and 4 vessel diameters removed from the thrombus.

41. The method of claim 39, wherein the ultraviolet laser beam is directed onto the vessel by transmission through an optical fiber or a liquid core optical guide.

42. A method for dissolving a thrombus in a blood vessel of a mammal, comprising the step of:

directing an ultraviolet laser beam onto an external or internal surface of the blood vessel within about 20 vessel diameters of the thrombus but not impinging on the thrombus, wherein the illuminated portion of the vessel is essentially free of blood at the time of illumination, wherein the vessel dilates during or following exposure to the laser beam, whereby the thrombus subsequently dissolves.

43. A method for dissolving a thrombus in a blood vessel of a mammal, comprising the step of:

directing a pulsed ultraviolet laser beam onto an external or internal surface of the blood vessel within about 20 vessel diameters of the thrombus but not impinging on the thrombus, wherein the energy fluence per pulse is less than 1 joule/cm$^2$, wherein the vessel dilates during or following exposure to the laser beam, whereby the thrombus subsequently dissolves.

* * * * *

UNITED STATES PATENT AND TRADEMARK OFFICE
CERTIFICATE OF CORRECTION

PATENT NO. : 6,539,944 B1 Page 1 of 1
DATED : April 1, 2003
INVENTOR(S) : Brant D. Watson It is certified that error appears in the above-identified patent and that said Letters Patent is hereby corrected as shown below:

Title page,
Item [56], References Cited, OTHER PUBLICATIONS, Third Reference, "haemorrage" has been replaced with -- hemorrhage --; Sixth Reference, -- 1992 -- has been inserted before "1447-1456"; Seventh Reference, -- 1994 -- has been inserted before "pp. PL 1-4"; Ninth Reference, "Dow Gal" has been replaced with -- Dov Gal --; Eleventh Reference, "84" has been removed; Twelfth Reference, -- 1993 -- has been inserted before "pp. 661-669 --; Fourteenth Reference, "r-Hiroudin" has been replaced with -- r-Hirudin --; Seventeenth Reference, "Histoshi" has been replaced with -- Hitoshi --;

Column 5,
Line 30, "irradiation of 355 nm" has been replaced with -- radiation of 355 nm --;
Lines 39 and 40, "UW" has been replaced with -- UV --;

Column 6,
Line 27, "mJ/mm$^{2/}$pulse" has been replaced with -- mJ/mm$^2$/pulse --;

Column 8,
Line 13, "GPIIIa-IIb" has been replaced with -- GPIIb-IIIa --;

Column 9,
Lines 46-47, "(n-1($\theta_{out}$," has been replaced with -- (n-1)$\theta_B$ --;

Column 14,
Line 25, "Bimgruber" has been replaced with -- Birngruber --;
Line 53, -- 1961 -- has been inserted before "44:499-519";

Column 16,
Line 27, "uroliase" has been replaced with -- urokinase --.

Signed and Sealed this

Fourteenth Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,539,944 B1
DATED : April 1, 2003
INVENTOR(S) : Brant D. Watson It is certified that error appears in the above-identified patent and that said Letters Patent is hereby corrected as shown below:

<u>Column 1,</u>
Line 6, insert the following:
-- This invention was made using funds from the U.S. government. The government retains certain right in the invention according to the terms of NIH grant No. NS23244. --.

Signed and Sealed this

Sixteenth Day of May, 2006

JON W. DUDAS
*Director of the United States Patent and Trademark Office*